US012643840B2

(12) United States Patent
Sandacz et al.

(10) Patent No.: US 12,643,840 B2
(45) Date of Patent: Jun. 2, 2026

(54) APPARATUS AND PROCESS FOR DISTRIBUTING QUENCH FLUID

(71) Applicant: UOP LLC, Des Plaines, IL (US)

(72) Inventors: Michael S. Sandacz, Glen Ellyn, IL (US); Sathit Kulprathipanja, Schaumburg, IL (US)

(73) Assignee: UOP LLC, Rosemont, IL (US)

( * ) Notice: Subject to any disclaimer, the term of this patent is extended or adjusted under 35 U.S.C. 154(b) by 442 days.

(21) Appl. No.: 18/136,753

(22) Filed: Apr. 19, 2023

(65) Prior Publication Data

US 2023/0416172 A1     Dec. 28, 2023

Related U.S. Application Data

(60) Provisional application No. 63/355,131, filed on Jun. 24, 2022.

(51) Int. Cl.
| | |
|---|---|
| *C07C 5/48* | (2006.01) |
| *B01J 4/00* | (2006.01) |
| *B01J 8/00* | (2006.01) |
| *B01J 8/18* | (2006.01) |

(52) U.S. Cl.
CPC ................. *C07C 5/48* (2013.01); *B01J 8/005* (2013.01)

(58) Field of Classification Search
CPC .. C07C 5/48; B01J 8/0055; B01J 8/005; B01J 8/1836; B01J 8/26; B01J 2208/00362; B01J 4/002
See application file for complete search history.

(56) References Cited

U.S. PATENT DOCUMENTS

| | | | | |
|---|---|---|---|---|
| 5,087,349 A | * | 2/1992 | Goelzer | C10G 11/18 |
| | | | | 208/159 |
| 5,302,280 A | * | 4/1994 | Lomas | C10G 11/18 |
| | | | | 208/113 |
| 5,954,942 A | * | 9/1999 | Adornato | C10G 11/18 |
| | | | | 208/103 |
| 2010/0137662 A1 | * | 6/2010 | Sechrist | C10G 45/02 |
| | | | | 585/240 |
| 2016/0362351 A1 | * | 12/2016 | Nagaki | B01J 23/745 |
| 2022/0032250 A1 | | 2/2022 | Senetar et al. | |
| 2022/0033326 A1 | | 2/2022 | Davydov et al. | |
| 2022/0333018 A1 | | 10/2022 | Senetar et al. | |

FOREIGN PATENT DOCUMENTS

| | | |
|---|---|---|
| CN | 104342192 A | 2/2015 |
| CN | 112538381 B | 3/2021 |

OTHER PUBLICATIONS

Search Report and Written Opinion for PCT/US2023/02611 dated Oct. 12, 2023.

* cited by examiner

*Primary Examiner* — In Suk C Bullock
*Assistant Examiner* — Jason Y Chong
(74) *Attorney, Agent, or Firm* — Paschall & Associates, LLC; James C. Paschall

(57)     ABSTRACT

A process for distributing quench fluid to a stream of product comprising contacting a feed stream with a stream of catalyst to convert the feed stream to product. The quench fluid is sprayed into the stream of product from a first distributor through at least one first opening centered at a first radial position and from a second distributor through at least one second opening centered at a second radial position different from the first radial position. Catalyst is preferably separated from the product stream prior to quenching. The process may include a first set of first distributors and a second set of second distributors.

14 Claims, 3 Drawing Sheets

APPARATUS AND PROCESS FOR DISTRIBUTING QUENCH FLUID

CROSS-REFERENCE TO RELATED APPLICATIONS

This application claims priority from U.S. Provisional Application No. 63/355,131, filed Jun. 24, 2022, which is incorporated herein in its entirety.

FIELD

The field is the reaction of feed with fluid catalyst. The field particularly relates to distributing quench fluid to a product stream.

BACKGROUND

Light olefin production is vital to the production of sufficient plastics to meet worldwide demand. Paraffin dehydrogenation (PDH) is a process in which light paraffins such as ethane and propane can be dehydrogenated to make ethylene and propylene, respectively. Dehydrogenation is an endothermic reaction which requires external heat to drive the reaction to completion.

Dehydrogenation catalyst may incorporate a dehydrogenation metal with a molecular sieve or an amorphous material. The catalyst must be sufficiently robust and appropriately sized to be able to resist the attrition expected in a fluidized system.

In PDH reactions with fluidized catalyst, coke can deposit on the catalyst while catalyzing the reaction. The catalyst may be regenerated in a catalyst regenerator by combusting coke from the catalyst in the presence of oxygen. The hot regenerated catalyst may then be transferred back to the reactor to catalyze the reaction. If insufficient heat is provided to drive the endothermic reaction, olefin production can suffer.

Both catalytic reactions and thermal cracking reactions can occur in a catalytic reactor at elevated temperature. The catalytic reactions are more selective to the desired products such as propylene than the thermal cracking reactions. Care must be taken to maximize catalytic reactions over thermal cracking reactions to improve selectivity to propylene. When the catalyst is separated from product, the product can still be at high temperature. Conditions at this point can favor thermal cracking reactions over catalytic reactions. The reactor product can be rapidly cooled by quenching to terminate thermal cracking reactions which can crack propylene product to undesirable lighter gaseous products.

There is a need, therefore, for improved methods of contacting catalyst with quench fluid in a fluidized catalytic reaction process.

BRIEF SUMMARY

The disclosure pertains to a process for distributing quench fluid to a stream of product. The process involves contacting a feed stream with a stream of catalyst to convert the feed stream to product. The quench fluid is sprayed into the stream of product from a first distributor through at least one first opening centered at a first radial position and from a second distributor through at least one second opening centered at a second radial position different from the first radial position. Catalyst is preferably separated from the product stream prior to quenching. The process may include a first set of first distributors with at least one first opening centered at a first radial position and a second set of second distributors with at least one second opening centered at a second radial position from a center of the vessel that is different from the first radial position.

Additional details and embodiments of the invention will become apparent from the following detailed description of the invention.

DEFINITIONS

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

As used herein, the term "predominant" or "predominate" means greater than 50%, suitably greater than 75% and preferably greater than 90%.

DETAILED DESCRIPTION

In a fluidized PDH reactor, dehydrogenation catalyst and olefinic product gases are separated from each other in a primary catalyst separator. More than 90 wt % of dehydrogenation catalyst can be separated by the primary catalyst separator. A quench injection may be used to cool down the reactor effluent as quickly as possible at an outlet of a primary catalyst separator to maintain the targeted product selectivity and minimize propane consumption. Ensuring good atomization of the fluid to adequately distribute the quench fluid for good contact with the product gas to adequately reduce its temperature is a challenge due to the large cross-sectional area of the duct transporting the product gas with the entrained catalyst remaining from the initial separation and the high velocity of the product gas.

PDH catalyst is used in a dehydrogenation reaction process to catalyze the dehydrogenation of paraffins, such as propane, iso-butane, and n-butane, to olefins, such as propylene, isobutene and n-butenes, respectively. The conditions in the dehydrogenation reactor may include a temperature of about 500 to about 800° C., a pressure of about 40 to about 310 kPa and a catalyst to oil ratio of about 5 to about 100. The dehydrogenation reaction may be conducted in a fluidized manner such that gas, which may be the reactant paraffins with or without a fluidizing inert gas, is distributed to the reactor in a way that lifts the dehydrogenation catalyst in the reactor vessel while catalyzing the dehydrogenation of paraffins. During the catalytic dehydrogenation reaction, coke is deposited on the dehydrogenation catalyst leading to reduction of the activity of the catalyst. The dehydrogenation catalyst must then be regenerated.

Figure 1:
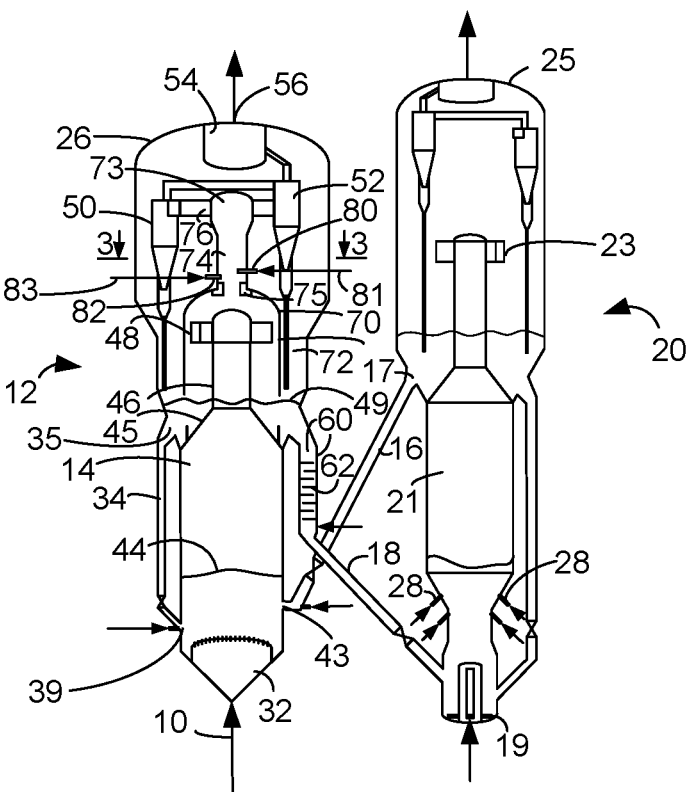
FIG. 1 is a schematic view of a conversion unit of the present disclosure.

An exemplary PDH reactor 12 is shown in FIG. 1. The PDH reactor 12 may comprise two chambers, a reaction chamber 14 and a separation chamber 26. A feed line 10 may charge a feed stream to the reactor 12. The feed stream may predominantly comprise propane or butane, but other paraffins such as ethane may be present in the feed stream in conjunction with or to the exclusion of other paraffins. Any feed distributor can distribute the feed stream to the reactor 12. A domed reactant distributor 32 or a pipe grid distributor may be utilized in the reaction chamber 14 of the reactor 12. The depicted domed reactant distributor 32 receives a gaseous feed stream and distributes the feed stream through nozzles in the top dome of the domed reactant distributor 32 to distribute the feed stream across the entire cross section of the reaction chamber 14. It is envisioned that other fluidizing gases may be used to also promote fluidization in the reaction chamber 14. In an embodiment, the distributed feed stream ascends in the reaction chamber 14 and the reactor 12.

A recycle catalyst pipe 34 has an inlet 35 located in the separation chamber 26 and an outlet comprising a first catalyst inlet 39 in the reaction chamber 14. The recycle catalyst pipe 34 delivers a first stream of recycled spent catalyst that has not undergone regeneration from the separation chamber 26 through the outlet and the first catalyst inlet 39 to the reaction chamber 14. The first catalyst inlet 39 provides spent catalyst to the reaction chamber 14.

To supply additional heat and catalyst to the reaction chamber 14, a second catalyst inlet 43 delivers a second catalyst stream to the reactor 12. A regenerated catalyst pipe 16 has an inlet 17 located in a regenerator 20 and an outlet connected to the second catalyst inlet 43 in the reaction chamber 14. The regenerated catalyst pipe 16 delivers a second stream of regenerated catalyst from the regenerator 20 through the outlet to the second catalyst inlet 43. In an embodiment, the feed stream may be contacted with the second catalyst stream after contacting the feed stream with the first catalyst stream.

The regenerated catalyst has just undergone combustive regeneration, has a very hot average temperature and is active since coke deposits have been combusted from its surface. Hence in the reaction chamber 14, the feed stream is provided with additional enthalpy and catalyst to catalytically convert paraffins to olefins, typically propane to propylene. The average temperature of the second stream of catalyst may be about 500 to about 900° C. Consequently, the temperature of the reaction chamber 14 may be about 400 to about 800° C.

In the reaction chamber 14 the feed stream is contacted with the first stream of catalyst and the second stream of catalyst which mix together, and the reactant paraffins undergo conversion to olefins, typically propane to propylene. The feed stream and the catalyst streams rise in the reaction chamber 14 of the reactor 12 impelled by the feed stream continually entering the reactor through the reactant distributor 32. At the interface 44, the fluid dynamics transition from a dense phase of catalyst below the interface to a fast-fluidized flow regime above the interface. The catalyst density in the dense phase of catalyst is at least 200 kg/m$^3$ (12.5 lb/ft$^3$); whereas the catalyst density in the fast-fluidized flow regime is at least 100 kg/m$^3$ (6.3 lb/ft$^3$). The superficial velocity of the feed stream and the first stream of catalyst and the second stream of catalyst in the reaction chamber 14 will typically be at least about 0.9 m/s (3 ft/s), suitably at least about 1.1 m/s (3.5 ft/s), preferably at least 1.4 m/s (4.5 ft/s), to about 2.1 m/s (7 ft/s) to provide the fast-fluidized flow regime. Reactant gas and catalyst ascend in a fast-fluidized flow regime in which catalyst may slip relative to the gas and the gas can take indirect upward trajectories.

The dehydrogenation catalyst may be of any of a variety of catalysts suitable for a fluidized dehydrogenation unit. The dehydrogenation catalyst selected should minimize cracking reactions and favor dehydrogenation reactions. Suitable catalysts for use herein include amorphous material or molecular sieves which may be dispersed in a porous inorganic carrier material such as silica, aluminum, zirconium, or clay. An exemplary embodiment of a catalyst includes crystalline silica-alumina or silica-alumina-phosphate as the primary active component, a matrix, a binder, and a filler.

The matrix component may include amorphous alumina or silica, and the binder and filler provide physical strength and integrity. Silica sol or alumina sol may be used as the binder and kaolin clay may be used as the filler. The catalyst particles may have a nominal diameter of about 20 to about 150 micrometers with the average diameter of about 70 to about 90 micrometers.

The dehydrogenation catalyst may support a dehydrogenation metal. The dehydrogenation metal may be a one or a combination of transition metals. A noble metal may be a preferred dehydrogenation metal; however, a IIB or a IIIB metal may be a suitable dehydrogenation metal alone or in combination with other dehydrogenation metals. Iron, tungsten, gallium, copper, zinc or zirconium alone or in combination with each other or a noble metal may be suitable dehydrogenation metals. Combustion promoters may be utilized in addition to the catalyst. Metals may be incorporated into the lattice structure of the molecular sieve.

The acid function of the catalyst should be minimized to prevent cracking and favor dehydrogenation. Alkali metals and alkaline earth metals may also be included in the catalyst to attenuate the acidity of the catalyst. Rare earth metals may be included in the catalyst to control the activity of the catalyst. Concentrations of 0.05 to 10 wt % metals may be incorporated into the catalyst. In the case of the noble metals, such as platinum, it is preferred to use about 0.05 to about 2 wt % noble metal.

The feed stream lifts the first stream of catalyst mixed with the second stream of catalyst upwardly in the reaction chamber 14 while paraffins convert to olefins in the presence of the dehydrogenation catalyst which gradually becomes spent catalyst attributed to the agglomeration of coke deposits on the catalyst. A fluidizing inert gas may be distributed to the reaction chamber to assist in lifting the mixture of catalyst and reactants upwardly in the reaction chamber 14. The reactant gases convert to product gases while ascending in the reaction chamber 14. The blend of gases and catalyst ascend from the reaction chamber 14 through a frustoconical transition section 45 into a transport riser 46 which has a smaller diameter than the diameter of the reaction chamber 14. The separation chamber 26 is in downstream communication with the reaction chamber 14 through the riser 46. A blend of gases and catalyst accelerate in the narrower transport riser 46 and are discharged from a primary catalyst separator 48 into the separation chamber 26. The primary catalyst separator 48 may be a riser termination device that utilizes horizontal, centripetal acceleration to separate spent catalyst from product gas. Arcuate ducts of the primary catalyst separator 48 direct the mixture of olefinic product gas and spent catalyst to exit from the riser 46 in a typically horizontally angular direction to centripetally accelerate causing the denser catalyst to gravitate more outwardly than the less dense gas. The catalyst loses angular momentum and falls into a lower catalyst bed 49 depicted with an upper interphase. The lighter gases ascend in the separation chamber 26.

The separation chamber 26 may include a disengagement chamber 70 that surrounds the upper end of the riser 46 and the primary separator 48. A vertical wall of the disengagement can 70 is spaced apart from a shell of the separation chamber 26 of the reactor 12 to define an annulus 72 therebetween. Dip legs of the cyclones 50 and 52 may be located in the annulus 72. The disengagement chamber 70 contains and confines the olefinic product gas in a contained space that may be defined by the vertical wall of the disengagement can. The contained space has a volume that is smaller than the volume of the reactor 12, and specifically, smaller than the reaction chamber 26, at the same elevation. The disengagement can 70 serves to limit travel of the product gas exiting the primary separator 48 at reactor temperature, so as to reduce its time in the reactor 12, thereby mitigating unselective cracking reactions to undesired products.

The top of the disengagement can 70 may be hemispherical or conical and feed a gas recovery conduit 74 extending from a center of the top of the disengagement can. The gas recovery conduit 74 is contiguous with the disengagement chamber 70. The gas recovery conduit 74 transports olefinic product gases to a distribution plenum 73. To minimize unselective thermal cracking to lower value by-products, the product gases are quenched with quench fluid from a distributor 80 fed by line 81 and a second distributor 82 fed by line 83 to cool the product gas to below thermal cracking temperature. Quenching may be conducted in the disengagement chamber 70 or in the gas recovery conduit 74. The first distributor 80 and the second distributor 82 may be located in the disengagement chamber 70 above the primary separator 48 but below gas recovery conduit 74. The preferred design criterion is that quench is performed downstream of separation, so a smaller mass of material must be quenched.

The quench fluid is sprayed into the stream of product from the first distributor 80 with a first tip at a first radial position from an axial center of the gas recovery conduit 74 and from a second distributor 82 with a second tip at a second radial position from an axial center of the gas recovery conduit which is different from the first radial position. The first tip of the first distributor 80 may be at a higher elevation than the second tip of the second distributor 82. The first distributor 80 and the second distributor 82 may have their tips in the disengagement chamber 70 or in the gas recovery conduit 74 downstream of the primary separator 48.

The first distributor 80 and the second distributor 82 in FIG. 1 have a horizontal configuration, but an upwardly or a downwardly angled configuration may also be suitable. A downwardly directed first distributor 80 and a downwardly directed second distributor 82 mounted in the gas recovery conduit 74 or the disengagement chamber 70 may spray quench fluid downwardly into the disengagement chamber 70.

Baffles 75 may be installed in the confluence between the disengagement chamber 70 and the gas recovery conduit 74 to impede and mitigate the swirling of the product gas stream centripetally discharged from the primary separator 48. Baffles 75 should be located downstream of the primary separator 48.

Quench fluid may comprise solvent and recovered catalyst. The quench fluid with the quenched product may pass through primary cyclones 50 and secondary cyclones 52. The solvent may be heavier in molecular weight than the lighter molecular weight product. The solvent may be laden with a light load of catalyst comprising a slurry oil. Quenching the product gas with the solvent slurry oil returns the catalyst in the slurry oil to the catalyst inventory in the reactor 12. The solvent may be an aromatic oil such as comprising C9 to C12 aromatic hydrocarbons.

Ducts 76 are directly ducted or connected between the distribution plenum 73 and the primary cyclones 50. The direct ducting from the disengagement chamber 70 to the primary cyclones 50 also prevents product gas from getting loose in the larger volume of the separation chamber 26 where excessive residence time may occur to permit unselective thermal cracking. Dehydrogenation catalyst separated from the olefinic product gas by the primary catalyst separator 48 drops into the dense catalyst bed 49 in the separation chamber 26.

The cyclones 50, 52 may comprise first and second cyclonic stages of separation to further remove catalyst from product gases. The olefinic product gas is ducted to a plenum 54 from which it is discharged from the reactor 12 through a product outlet 56 in a product line. The superficial gas velocity in the transport riser 46 will be about 12 m/s (40 ft/s) to about 20 m/s (70 ft/s) and have a density of about 64 kg/m³ (4 lb/ft³) to about 160 kg/m³ (10 lb/ft³), constituting a dilute catalyst phase.

Catalyst separated from the product gas by the primary catalyst separator 48 drops into a dense catalyst bed 49. In an aspect, primary cyclones 50 may collect product gas from the gas recovery conduit 74 and transport the product gas separated from catalyst to a secondary cyclone 52 to further separate catalyst from the product gas before directing secondarily purified product gas to the plenum 54. Catalyst separated from product gas in the cyclones 50, 52 is dispensed by dip legs into the dense catalyst bed 49. At this point, the separated catalyst in the separation chamber 26 is considered spent catalyst because deposits of coke are agglomerated thereon.

A regeneration portion of the spent catalyst collected in the dense bed 49 in the separation chamber 26 is transported in a spent catalyst pipe 18 to a catalyst regenerator 20 to have coke burned from the catalyst to regenerate and heat the dehydrogenation catalyst. A vertical section of the spent catalyst pipe 18 may comprise a stripping section 60. A stripping gas such a steam or another inert gas may be fed into a lower end of the stripping section 60 to strip hydrocarbons from the spent catalyst entering the stripping section 60. Baffles 62 may also be provided in the stripping section 60 to cause the spent catalyst to wend laterally in the stripping section to expose more catalyst particles to upwardly flowing stripping gas. Baffles 62 could be replaced with packing, and/or gratings perhaps with downcomers to promote contact between the catalyst and stripping gas.

A recycle portion of the spent catalyst collected in the dense bed 49 of the separation chamber 26 enters the recycle catalyst pipe 34 through the inlet 35. The recycle portion of the spent catalyst is recycled in the recycle catalyst pipe 34 back to the first catalyst inlet 39 to the reaction chamber 14 of the reactor 12 as the first catalyst stream. The recycle portion of the spent catalyst is not regenerated before it returns to the reaction chamber 14.

Diplegs of the cyclones 50, 52, respectively, dispense spent dehydrogenation catalyst to the dense dehydrogenation catalyst bed 49 in the annulus 72. Openings in the lower section of the wall of the disengagement chamber 70 permit catalyst confined in the disengagement chamber to move into the annulus 72 and enter into the recycle catalyst pipe 34 or the regeneration pipe 18.

The first quench distributor 80 and the second quench distributor 82 may be in upstream communication with the gas recovery conduit 74 in the disengagement chamber 70. The gas recovery conduit 74 is in downstream communication with the primary catalyst separator 48 which separates the predominance of the spent catalyst from the product gases. The spent catalyst bypasses quenching to retain heat in the catalyst. The product gases separated from the predominance of the catalyst subjects a reduced mass of material to quenching thereby requiring less volume of quench fluid to achieve sufficient cooling to reduce the temperature of product gas to below thermal cracking temperature. The operation of the disengagement chamber 70 enables containment and capture of olefinic product gases and a vastly reduced mass of catalyst. The gas recovery conduit 74 directs the olefinic product gas to a narrowed location from the disengagement chamber 70 to effectively expose it to a quench material injected into the gas recovery conduit. The quench material may be water or hydrocarbon, such as paraffins recovered from a downstream dehydrogenation product recovery process.

The stripped, spent dehydrogenation catalyst is transported by the spent catalyst pipe 18 to the regenerator 20 to combust the coke on the spent catalyst and regenerate the spent catalyst into regenerated catalyst. The catalyst regenerator 20 includes a combustion chamber 21 and a catalyst separator 23 which separates regenerated catalyst from flue gas generated in the combustion chamber 21 as they are discharged from the catalyst separator 23. An oxygen supply gas is provided to the combustion chamber 21 through a distributor 19 which lifts the spent catalyst in the combustion chamber 21 through the catalyst separator 23 and into a separation chamber 25. The coke is burned off the spent catalyst by contact with the oxygen supply gas at regeneration conditions. In an exemplary embodiment, air is used as the oxygen supply gas, because air is readily available and provides sufficient oxygen for combustion. About 10 to about 15 kg of air are required per kg of coke burned off of the spent catalyst. Exemplary regeneration conditions include a temperature from about 500° C. (900° F.) to about 900° C. (1700° F.) and a pressure of about 103 kPa (abs) (15 psia) to about 450 kPa (abs) (70 psia) in the regenerator 20. Hydrocarbon fuel may be added to the regenerator 20 such as through nozzles 28 to boost the heat generated in the regenerator to drive the reaction in the reactor 12.

Regenerated catalyst is returned to the reactor 12 in the regenerated catalyst pipe 16. The regenerated catalyst pipe 16 has an inlet 17 connected to the regenerator 20 in the separation chamber 25 through which regenerated catalyst from the regenerator is transported to the second catalyst inlet 43 in the reactor 12 as the hotter second stream of catalyst. The regenerated catalyst is fed to the reactor 12 through the second catalyst inlet 43 which is the outlet of the regenerated catalyst pipe 16. The regenerated catalyst pipe 16 is connected to the second catalyst inlet 43.

Figure 2:
FIG. 2 is an enlarged, partial plan view of FIG. 1 taken at segment 3-3.

FIG. 2 is a partial sectional plan view that shows the first distributor 80 and the second distributor 82 that deliver droplets across a greater cross-section of the gas recovery conduit 74 to provide an even distribution of quench fluid across the cross-section.

The first distributor 80 and the second distributor 82 are illustrated protruding through a wall 122 of the gas recovery conduit 74 which may be made of steel and comprising an inner coating of a refractory lining 123. The first distributor 80 may comprise a first outer distributor barrel 124 which may be made of steel and coated with a refractory lining 125. The second distributor 82 may comprise a second distributor barrel 154 which may be made of steel and coated with a refractory lining 125. The first distributor 80 may comprise a first opening 130 for spraying hydrocarbon feed into the gas recovery conduit 74 or the disengagement chamber 70. The first distributor 80 may comprise a first cluster 126 of first openings 130 for spraying hydrocarbon feed into the gas recovery conduit 74 or the disengagement chamber 70. The first distributor 130 has a first center 150 of the first opening 130 or the first cluster 126 of first openings 130 located at a first radial position in the gas recovery conduit 74 relative to a longitudinal center C in the gas recovery conduit. The first center 150 of the first distributor 130 is the geometric center of the first opening 130 if there is only one first opening or of the first cluster 126 of first openings if a first cluster of first openings are provided on the first distributor 80. The second distributor 82 may comprise a second opening 131 for spraying hydrocarbon feed into the gas recovery conduit 74 or the disengagement chamber 70. The second distributor 82 may comprise a second cluster 127 of second openings 131 for spraying hydrocarbon feed into the gas recovery conduit 74 or the disengagement chamber 70. The second distributor 131 has a second center 151 of the second opening 131 or the second cluster 127 of second openings 131 located at a second radial position in the gas recovery conduit 74 relative to the longitudinal center C in the gas recovery conduit. The second center 151 of the second distributor 131 is the geometric center of the second opening 131 if there is only one second opening or of the second cluster 127 of second openings 131 if a second cluster of second openings are provided on the second distributor 82. The second radial position is different from the first radial position. The first radial position is more inward, farther from the wall 122 and closer to the center C, than the second radial position because the first distributor 80 is longer and extends further into the gas recovery conduit 74 than the second distributor 82. Alternatively, the first radial position may be at a different elevation than the second radial position. The first radial position may be different from the second radial position either in elevation or in distance from the center C.

The first radial position may represent a first radius from a center of the vessel on which the first cluster 127 of openings 131 is located and the second radial position may represent a second radius from the center of the vessel which is in this case, the gas recovery conduit 74, but it could be the disengagement chamber 70. The different radial positions may also be different because they have different elevations. In FIG. 1, the radial positions are different in elevation and in radius from center of the vessel. In FIG. 2, the radial position may be at the same elevation but have different radii from the center C of the gas recovery conduit 74.

The first openings 130 are orifices in the first distributor 80 that emit quench fluid into the gas recovery conduit 74. The second openings 131 are orifices in the second distributor 82 that emit quench fluid into the gas recovery conduit 74. The openings 130, 131 may be provided by small tubes 133 which impart direction and pattern to the spray of quench fluid from the respective opening. Additionally, the openings 130, 131 themselves may be configured to impart a desired trajectory to the spray of quench fluid emitted therefrom. The openings 130, 131 in a particular cluster 126, 127, respectively, may be configured together to cooperatively spray feed in a desired pattern, such as in a fan pattern. The openings 130, 131 may be round, such as circular or ovular, or may comprise slots.

In an embodiment, a first opening 130 or the first cluster 126 of first openings 130 may located on a first tip 132. In an embodiment, a second opening 131 or the second cluster 127 of second openings 131 may located on a second tip 137. The tips 132, 137 and the tubes 133 may be made of steel, or they may be made from a ceramic material or coated to resist erosion. The tips 132, 137 or the barrel 124, 154 may be removable from the distributor 80, 82, respectively, for replacement with a new tip or barrel, respectively. The first tip 132 may extend from the first distributor barrel 124. The second tip 137 may extend from the second distributor barrel 154.

FIG. 2 depicts tips 132, 137 with the first cluster 126 of first openings 130 and the second cluster 127 of second openings 131, respectively. The first cluster 126 of first openings 130 on the first tip 132 may be located on an inner end 136 of the first distributor 80. The inner end 136 of the first distributor 80 may protrude radially into the gas recovery conduit 74, so as to distribute droplets of quench fluid into an upwardly flowing stream of product gas. The second cluster 127 of second openings 131 on the second tip 137 may be located on an inner end 136 of the second distributor 82. The inner end 136 of the second distributor 82 may protrude radially into the gas recovery conduit 74, so as to distribute droplets of quench fluid into an upwardly flowing stream of product gas.

In one embodiment, a gas recovery conduit 74 may include a nozzle 135 for each distributor 80, 82. The nozzle 135 has a nozzle flange 139 that engages a barrel flange 123 of the distributor barrel 124, 154 with bolts. The distributor barrels 124, 154 receive an inert dispersion media stream such as steam or nitrogen from a dispersion media supply inlet 142 in downstream communication with a dispersion media supply. The distributor barrel 124, 154 also receives a quench fluid such as an aromatic solvent through a quench fluid supply inlet 144 in downstream communication with a quench fluid supply. The dispersion media travels in a first annulus 146 between a first internal quench pipe 148 and the first distributor barrel 124. The first cluster 126 of first openings 130 may be in downstream communication with the quench supply inlet 144 and the media supply inlet 142. Likewise, in the second distributor 82, the dispersion media travels in a second annulus 147 between a second internal quench pipe 149 and the second distributor barrel 154. The first cluster 126 of first openings 130 and the second cluster 127 of second openings 131 may be in downstream communication with the respective quench supply inlet 144 and the respective media supply inlet 142.

In the first distributor 80 an end conduit 138 extends from the first internal quench pipe 148 to the first tip 132 and transports a mixture of quench fluid from the internal quench pipe 148 to the first cluster 126 of first openings 130 on the first tip 132. In the second distributor 82, the end conduit 138 extends from the second internal quench pipe 149 to the second tip 137 and transports a mixture of quench fluid from the second internal quench pipe 149 to the second cluster 127 of second openings 131 on the end tip 137. The quench stream may pass from the first internal quench pipe 148 over vanes that may be in the end conduit 138 causing the quench fluid to swirl before mixing with the dispersion media entering from the annulus 146 through a port 134 in the first tip 132 and exiting through the openings 130 in the end cluster 126 on the first tip 132. The quench stream may pass from the second internal quench pipe 149 over vanes that may be in the end conduit 138 causing the quench fluid to swirl before mixing with the dispersion media entering from the annulus 147 through a port 134 in the second tip 137 and exiting through the second openings 131 in the second cluster 127 on the second tip 137. Several ports 134 may be utilized and located at a variety of locations. Mixing the dispersion gas with the quench liquid in the distributor 80, 82 atomizes the quench liquid sprayed from the distributor.

The first distributor 80 sprays quench fluid through first openings 130 centered at a first radial position into the stream of product gas and the second distributor 82 sprays quench fluid through second openings 131 centered at a second radial position different from the first radial position.

Figures 3, 4:
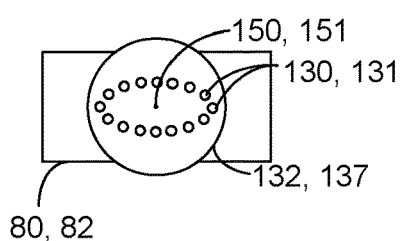
FIG. 3 is an end view of a distributor of FIG. 2.
FIG. 4 is an enlarged plan view of FIG. 1 taken at segment 3-3.

FIG. 3 shows the center 150, 151 for distributors 80, 82 of a cluster of openings 130, 131 on a distributor tip 132, 137, respectively. The openings 130, 131, for example, define an oval shaped cluster on the distributor tip 132, 137, respectively, which define a geometric center 150, 151. If only one opening 130, 131 is provided on the distributor tip 132, 137 for distributors 80, 82, the center 150, 151 would be the geometric center of the single opening 130, 131.

FIG. 4 illustrates a plan cross sectional view of the reactor 12 taken at segment 3-3 in FIG. 1 showing separation vessel 26, the disengagement chamber 70 and the gas recovery conduit 74. A first set or plurality 84 of first quench distributors 80 sprays the quench fluid into the stream of product gas from first openings 130 (FIG. 2) having centers at first radial positions located on an imaginary circle R1. The first set 84 of first distributors 80 have centers 150 are at the 3, 6, 9 and 12 'o' clock positions in the embodiment of FIG. 3. A second set or plurality 86 of second quench distributors 82 sprays the quench fluid into the stream of product gas from second openings 131 (FIG. 2) having centers 151 at second radial positions located on an imaginary circle R2 which is different from first radial positions located on the first imaginary circle R1. The first radial positions define the first imaginary circle R1, and the second radial positions define the second imaginary circle R2. The second set 86 of second quench distributors 82 are located at the 1, 2, 4, 5, 7, 8, 10 and 11 'o' clock positions in the embodiment of FIG. 3. The two imaginary circles R1 and R2 are concentrically centered at center C. The circles R1 and R2 may have different radiuses from the center C. The two imaginary circles R1 and R2 may also be set at different elevations at the same radial distance from the center C or at different elevations and different radial distances from the center. The first radial position represented by circle R1 may be different from the second radial position represented by circle R2 either in elevation or in distance from the center C.

Quench fluid from a first quench fluid pipe 90 supplies a first arcuate manifold 91 which supplies quench fluid supply inlets 144 (FIG. 2) of all of the first quench distributors 80 in the first set 84 of first distributors. Quench fluid from a second quench fluid pipe 92 supplies a second arcuate manifold 93 which supplies quench fluid supply inlets 144 (FIG. 2) of all of the second distributors 82 in the second set 86 of second quench distributors.

Dispersion media from a first dispersion media pipe 94 supplies a third arcuate manifold 95 which supplies dispersion media supply inlets 142 (FIG. 2) of all of the first quench distributors 80 in the first set 84 of first distributors. Dispersion media from a second quench fluid pipe 96 supplies a second arcuate manifold 97 which supplies quench fluid supply inlets 142 (FIG. 2) of all of the second distributors 82 in the second set 86 of second quench distributors.

The arrangement of the first set 84 of 2 to 16 first distributors of which 4 are shown spraying atomized quench fluid from first openings 130 (FIG. 2) from inner radial positions on circle R1 and the second set 86 of 4 to 20 second distributors of which 8 are shown spraying atomized quench fluid from second openings 131 (FIG. 2) from outer radial positions on R2 distributes quench fluid over a more complete cross section of the gas recovery conduit 74 to assure more rapid and thorough quenching of the product gas that has been separated from the bulk of the catalyst perhaps by centripetal separation.

SPECIFIC EMBODIMENTS

While the following is described in conjunction with specific embodiments, it will be understood that this description is intended to illustrate and not limit the scope of the preceding description and the appended claims.

A first embodiment of the invention is a process for distributing quench fluid to a stream of product comprising contacting a feed stream with a stream of catalyst to convert the feed stream to product; and spraying the quench fluid into the stream of product from a first distributor through at least one first opening having a first center at a first radial position and from a second distributor through at least one second opening having a second center at a second radial position different from the first radial position. An embodiment of the invention is one, any or all of prior embodiments in this paragraph up through the first embodiment in this paragraph further comprising mixing a gas with the quench liquid in a first distributor to atomize the quench liquid sprayed from the first distributor. An embodiment of the invention is one, any or all of prior embodiments in this paragraph up through the first embodiment in this paragraph further comprising spraying quench fluid into the stream of product after catalyst is separated from the stream of product. An embodiment of the invention is one, any or all of prior embodiments in this paragraph up through the first embodiment in this paragraph further comprising spraying the quench fluid into the stream of product from a first distributor through first openings having the first center at a first radial position and from a second distributor through second openings having the second center at a second radial position different from the first radial position. An embodiment of the invention is one, any or all of prior embodiments in this paragraph up through the first embodiment in this paragraph further comprising separating the product stream from a catalyst stream by centripetal acceleration. An embodiment of the invention is one, any or all of prior embodiments in this paragraph up through the first embodiment in this paragraph further comprising impeding the product stream from swirling upstream of quenching. An embodiment of the invention is one, any or all of prior embodiments in this paragraph up through the first embodiment in this paragraph wherein the quench fluid comprises catalyst discharged from the reactor in a liquid. An embodiment of the invention is one, any or all of prior embodiments in this paragraph up through the first embodiment in this paragraph catalyst in the quench fluid is returned to a catalyst inventory in the reactor. An embodiment of the invention is one, any or all of prior embodiments in this paragraph up through the first embodiment in this paragraph further comprising spraying the quench fluid from the first distributor with a horizontal trajectory. An embodiment of the invention is one, any or all of prior embodiments in this paragraph up through the first embodiment in this paragraph further comprising a plurality of first distributors with a first opening having first centers at first radial positions that define a first imaginary circle and a plurality of second distributors with a second opening having second centers at second radial positions that define a second imaginary circle that is different from the first imaginary circle. An embodiment of the invention is one, any or all of prior embodiments in this paragraph up through the first embodiment in this paragraph wherein the first distributor is at an elevation above an elevation of the second distributor.

A second embodiment of the invention is a process for distributing quench fluid to a stream of product comprising contacting a feed stream with a stream of catalyst to convert the feed stream to product; mixing a gas with the quench liquid in a first distributor to atomize the quench liquid; and spraying the quench fluid into the stream of product from the first distributor. An embodiment of the invention is one, any or all of prior embodiments in this paragraph up through the second embodiment in this paragraph further comprising spraying quench from the first distributor through at least one first opening centered at a first radial position and from a second distributor through at least one second opening centered at a second radial position different from the first radial position. An embodiment of the invention is one, any or all of prior embodiments in this paragraph up through the second embodiment in this paragraph further comprising separating the product stream from a catalyst stream by centripetal acceleration. An embodiment of the invention is one, any or all of prior embodiments in this paragraph up through the second embodiment in this paragraph wherein the quench fluid comprises catalyst discharged from the reactor in a liquid. An embodiment of the invention is one, any or all of prior embodiments in this paragraph up through the second embodiment in this paragraph catalyst in the quench fluid is returned to a catalyst inventory in the reactor. An embodiment of the invention is one, any or all of prior embodiments in this paragraph up through the second embodiment in this paragraph further comprising spraying the quench fluid from the first distributor with a horizontal trajectory. An embodiment of the invention is one, any or all of prior embodiments in this paragraph up through the second embodiment in this paragraph further comprising a plurality of first distributors with first openings centered at the first radial position and a plurality of second distributors with second openings centered at the second radial position.

A third embodiment of the invention is a process for distributing quench fluid to a stream of product comprising contacting a feed stream with a stream of catalyst to convert the feed stream to product; and spraying the quench fluid into the stream of product from a first set of first distributors through first openings having first centers at first radial positions and from a second set of second distributors through second openings having second centers at second radial positions different from the first radial positions. An embodiment of the invention is one, any or all of prior embodiments in this paragraph up through the third embodiment in this paragraph further comprising spraying quench fluid into the stream of product after catalyst is separated from the stream of product. An embodiment of the invention is one, any or all of prior embodiments in this paragraph up through the third embodiment in this paragraph further comprising separating the product stream from a catalyst stream by centripetal acceleration.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for distributing a quench fluid to a stream of product comprising:

contacting a feed stream with a stream of catalyst in a reaction chamber of a reactor to convert the feed stream to the stream of product, wherein the stream of product moves upwardly in the reactor; and quenching the stream of product in a quenching chamber of the reactor by spraying the quench fluid into the stream of product from a plurality of first distributors and a plurality of second distributors, wherein each of the first and second distributors has at least one opening and a center of the at least one opening, wherein the centers of the first distributors are located at first radial positions that define a first imaginary circle, and the centers of the second distributors are located at second radial positions that define a second imaginary circle, and wherein the second imaginary circle is different from the first imaginary circle.

2. The process of claim 1 further comprising mixing a gas with the quench liquid in the first distributors to atomize the quench liquid sprayed from the first distributors.

3. The process of claim 1 further comprising spraying the quench fluid into the stream of product after the catalyst is separated from said stream of product.

4. The process of claim 3 wherein the quench fluid comprises a portion of the catalyst discharged from the reactor in a liquid.

5. The process of claim 4 the catalyst in the quench fluid is returned to a catalyst inventory in the reactor.

6. The process of claim 3 further comprising spraying the quench fluid from the first distributors with a horizontal trajectory.

7. The process of claim 6 further comprising separating the product stream from a catalyst stream by centripetal acceleration.

8. The process of claim 1 further comprising impeding the product stream from swirling upstream of the quenching.

9. The process of claim 1 wherein the first distributors are at an elevation above an elevation of the second distributors.

10. The process of claim 9 wherein the quench fluid comprises a portion of the catalyst discharged from the reactor in a liquid.

11. The process of claim 10 the catalyst in the quench fluid is returned to a catalyst inventory in the reactor.

12. The process of claim 1 further comprising separating the product stream from a catalyst stream by centripetal acceleration.

13. A process for distributing a quench fluid to a stream of product comprising:

contacting a feed stream with a stream of catalyst in a reaction chamber of a reactor to convert the feed stream to the stream product, wherein the stream of product moves upwardly in the reactor;

mixing a gas with the quench liquid in a plurality of first distributors and a plurality of second distributors to atomize the quench liquid; and quenching the stream of product in a quenching chamber of the reactor by spraying the quench fluid into the stream of product from the plurality of first distributors the plurality of second distributors, wherein each of the first and second distributors has at least one opening and a center of the at least one opening, wherein the centers of the first distributors are located at first radial positions that define a first imaginary circle, and the centers of the second distributors are located at second radial positions that define a second imaginary circle, and wherein the second imaginary circle is different from the first imaginary circle.

14. The process of claim 13 further comprising spraying the quench fluid from the first distributors with a horizontal trajectory.

* * * * *